United States Patent
Krimsky et al.

(10) Patent No.: US 10,239,802 B2
(45) Date of Patent: Mar. 26, 2019

(54) PROCESSES AND APPARATUSES FOR TOLUENE METHYLATION IN AN AROMATICS COMPLEX

(71) Applicant: UOP LLC, Des Plaines, IL (US)

(72) Inventors: David S. Krimsky, Cypress, TX (US); Robert B. Larson, Lisle, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/989,084

(22) Filed: May 24, 2018

(65) Prior Publication Data
US 2018/0265429 A1    Sep. 20, 2018

Related U.S. Application Data

(63) Continuation of application No. PCT/US2016/064306, filed on Dec. 1, 2016.
(Continued)

(51) Int. Cl.
*C07C 6/00* (2006.01)
*C07C 6/12* (2006.01)
(Continued)

(52) U.S. Cl.
CPC .............. *C07C 6/126* (2013.01); *C07C 2/864* (2013.01); *C07C 4/18* (2013.01); *C07C 5/222* (2013.01);
(Continued)

(58) Field of Classification Search
CPC ......... C07C 15/08; C07C 6/123; C07C 15/04; C07C 15/06; C07C 15/067;
(Continued)

(56) References Cited

U.S. PATENT DOCUMENTS 6,740,788 B1    5/2004 Maher et al.
7,638,669 B2 *  12/2009 Casey .................. C07C 5/2702
                                                585/470
(Continued)

FOREIGN PATENT DOCUMENTS

CN     102190553 A    9/2011
CN     101993333 B    1/2014
(Continued)

OTHER PUBLICATIONS

Kollar, Marton et al., "Transformations of Alkyl aromatics over delaminated MCM-22 zeolites and their composites with mesoporous MCM-41 silicate", Applied Catalysis A: General, v 393, n 1-2, p. 59-70, Feb. 15, 2011; ISSN: 0926860X; DOI: 10.1016/j.apcata.2010.11.024; Publisher: Elsevier.
(Continued)

*Primary Examiner* — Sharon Pregler

(57) ABSTRACT

This present disclosure relates to processes and apparatuses for toluene methylation in an aromatics complex for producing paraxylene. More specifically, the present disclosure relates to processes and apparatuses wherein a toluene methylation zone is integrated within an aromatics complex for producing paraxylene thus allowing no benzene byproduct to be produced. This may be accomplished by incorporating a toluene methylation process into the aromatics complex and recycling the benzene to the transalkylation unit the aromatics complex.

18 Claims, 4 Drawing Sheets

Related U.S. Application Data

(60) Provisional application No. 62/267,966, filed on Dec. 16, 2015.

(51) Int. Cl.
| | |
|---|---|
| *C07C 2/86* | (2006.01) |
| *C07C 5/22* | (2006.01) |
| *C07C 7/08* | (2006.01) |
| *C07C 7/12* | (2006.01) |
| *C10G 29/20* | (2006.01) |
| *C10G 69/12* | (2006.01) |
| *C07C 4/18* | (2006.01) |
| *C07C 5/27* | (2006.01) |

(52) U.S. Cl.
CPC ............ *C07C 5/277* (2013.01); *C07C 5/2737* (2013.01); *C07C 7/08* (2013.01); *C07C 7/12* (2013.01); *C10G 29/205* (2013.01); *C10G 69/123* (2013.01); *C10G 2400/30* (2013.01)

(58) Field of Classification Search
CPC C10G 2400/30; C10G 29/205; C10G 69/123; C10G 35/04; C10G 2300/1044; C10G 35/00; C10G 21/00; C10G 2300/1096
See application file for complete search history.

(56) References Cited

U.S. PATENT DOCUMENTS 8,030,533 B2  10/2011  Hotier et al.
9,302,953 B2 *  4/2016  Molinier .............. B01J 19/2445

FOREIGN PATENT DOCUMENTS

| CN | 102040461 B | 7/2014 |
|---|---|---|
| KR | 2007068254 A | 6/2007 |
| KR | 2007110558 A | 11/2007 |
| WO | 2015142454 A1 | 9/2015 |

OTHER PUBLICATIONS

Nakamura, I. et al., "Disproportionation/isomerization of alkylbenzenes over USY zeolite mixed with supported metal sulfides", Sekiyu Gakkaishi (Journal of the Japan Petroleum Institute) (ISSN 0582-4664) V40 N.1 23-28 (Jan. 1997) (in Japanese with English abstract), v 40, n 1, p. 23-28, Jan. 1997; Language: Japanese; ISSN: 05824664; Publisher: Japan Petroleum Institute.

Mortikov, E. S. et al., "The disproportionation of xylenes over a cay zeolite catalyst", Neftepererab. Neftekhim. (Mosc.) N.10 28-29 (1975) (Transl.) Int. Chem. Eng. V18 N.1 86-87 (Jan. 1978), 1975; Language: Russian;English.

Roldan, R. et al., "Transformation of mixtures of benzene and xylenes into toluene by transalkylation on zeolites", Applied Catalysis A: General, v 266, n 2, p. 203-210, Jul. 20, 2004; ISSN: 0926860X; Publisher: Elsevier.

Dupraz, C. et al., "Integrating technologies for para-xylene production", Petroleum Technology Quarterly (ISSN 1362-363) V3 N.3 135-38,140-41 (Autumn 1998), v 3, n 3, p. 135-38,140-41, Sep. 1998; ISSN: 1362363X; Publisher: Crambeth Allen Publishing.

Gardos, G. et al., "Desalkylation of Alkyl-Aromatic Hydrocarbons II. Desalkylation of M-Xylene and A C9 Industrial Aromatic Mixture on Metal Oxide Catalysts", Hung. J. Ind. Chem. (ISSN 0133-0276) V14 N.4 403-9 (1986), v 14, n 4, p. 403-9, 1986; ISSN: 01330276; Publisher: University of Veszprem.

Takaya, "The Formation of High Boiling By-Products in the Isomerization and Disproportionation of M-Xylene Over a Silica-Alumina Catalyst Under Pressure", Bull Soc Chem Jap V45 N.8 2337-43 (Aug. 1972), Aug. 1972.

Olson, D. H. et al., "A Structure-Selectivity Relationship (was Observed) in Xylene Isomerization and Selective Toluene Disproportionation", ACS Div. Ind. Eng. Chem. 'Catal. Mater. Relationship Struct. Reactivity' Symp. (San Franc. Jun. 13-16, 1983) ACS Symp. Ser. N.248 275-307 (1984), Jun. 13, 1983.

Manoiu, D. et al., "Disproportionation of Toluene Simultaneously with Isomerization of M-Xylene on Synthetic H-Mordenite", Appl. Catal. 1(6) 383-6 (1981) Chem. Abstr. Abstr.No. 34203 V96 N.5, v 1, n 6, p. 383-6, 1981; ISSN: 01669834; Publisher: Elsevier.

PCT Search Report dated Mar. 16, 2017 for corresponding PCT Application No. PCT/US2016/064306.

* cited by examiner

PROCESSES AND APPARATUSES FOR TOLUENE METHYLATION IN AN AROMATICS COMPLEX

CROSS-REFERENCE TO RELATED APPLICATIONS

This application is a Continuation of copending International Application No. PCT/US2016/064306 filed Dec. 1, 2016, which application claims priority from U.S. Provisional Application No. 62/267,966 filed Dec. 16, 2015, the contents of which cited applications are hereby incorporated by reference in their entirety.

FIELD

This present disclosure relates to processes and apparatuses for toluene methylation in an aromatics complex for producing paraxylene. More specifically, the present disclosure relates to processes and apparatuses for toluene methylation within an aromatics complex for producing paraxylene where no benzene byproduct is produced.

BACKGROUND

The xylene isomers are produced in large volumes from petroleum as feedstocks for a variety of important industrial chemicals. The most important of the xylene isomers is paraxylene, the principal feedstock for polyester, which continues to enjoy a high growth rate from large base demand. Ortho-xylene is used to produce phthalic anhydride, which supplies high-volume but relatively mature markets. Meta-xylene is used in lesser but growing volumes for such products as plasticizers, azo dyes and wood preservers. Ethylbenzene generally is present in xylene mixtures and is occasionally recovered for styrene production, but is usually considered a less-desirable component of $C_8$ aromatics.

Among the aromatic hydrocarbons, the overall importance of xylenes rivals that of benzene as a feedstock for industrial chemicals. Xylenes and benzene are produced from petroleum by reforming naphtha but not in sufficient volume to meet demand, thus conversion of other hydrocarbons is necessary to increase the yield of xylenes and benzene. Often toluene is de-alkylated to produce benzene or selectively disproportionated to yield benzene and $C_8$ aromatics from which the individual xylene isomers are recovered.

An aromatics complex flow scheme has been disclosed by Meyers in the HANDBOOK OF PETROLEUM REFINING PROCESSES, 2d. Edition in 1997 by McGraw-Hill, and is incorporated herein by reference.

Traditional aromatics complexes send toluene to a transalkylation zone to generate desirable xylene isomers via transalkylation of the toluene with $A_{9+}$ components. $A_{9+}$ components are present in both the reformate bottoms and the transalkylation effluent.

Paraxylene is most often produced from a feedstock which has a methyl to phenyl ratio of less than 2. As a result, the paraxylene production is limited by the available methyl groups in the feed. In addition, paraxylene production also typically produces benzene as a byproduct. Since paraxylene is more valuable than benzene and the other byproducts produced in an aromatics complex, there is a desire to maximize the paraxylene production from a given amount of feed. There are also cases where a paraxylene producer would prefer to avoid the production of benzene as a byproduct or paraxylene production. However, there are also cases where a paraxylene producer would prefer to limit the production of benzene as a byproduct or paraxylene production by making adjustments.

SUMMARY

The present subject matter relates to processes and apparatuses for toluene methylation in an aromatics complex for producing paraxylene. More specifically, the present disclosure relates to processes and apparatuses for toluene methylation within an aromatics complex for producing paraxylene where no benzene byproduct is produced. Integrating a toluene methylation process within an aromatics complex has several benefits. First, the integrated process may increase the amount of paraxylene that can be produced form a given amount of reformate. The integrated process may also reduce the amount of reformate required to produce a fixed amount of paraxylene. Second, the integrated process may avoid the production of benzene as a byproduct from the aromatics complex. These two benefits may be accomplished by incorporating a toluene methylation process into the aromatics complex and recycling the benzene to the transalkylation unit the aromatics complex.

A first embodiment of the invention is a process for producing paraxylene with no benzene byproduct, comprising passing a lighter aromatic stream containing benzene and a heavier aromatic stream containing $C_9$-$C_{10}$ aromatic compounds to a transalkylation zone; subjecting the lighter aromatic stream and the heavier aromatic stream in the transalkylation zone to transalkylation conditions including the presence of a first catalyst to provide a transalkylation product stream having a greater concentration of toluene to $C_8$ aromatics; separating by fractionation from the transalkylation product stream a first boiling fraction comprising benzene, a second boiling fraction comprising toluene, a third boiling fraction comprising $C_8$ aromatics and a fourth boiling fraction comprising $C_{9+}$ aromatics; recycling at least a portion of the benzene from the transalkylation product stream back to the transalkylation zone; passing at least a portion of the second boiling fraction from steps c, g and i and a methanol stream to a toluene methylation zone operating under toluene methylation conditions to produce a toluene methylation product stream; separating by fractionation from the toluene methylation product stream the same fractions described in step c; subjecting at least a portion of the third boiling fraction comprising $C_8$ aromatics of steps c, g and i to a separation zone to selectively remove a paraxylene product and provide a non-equilibrium mixture of $C_8$ aromatics; passing the non-equilibrium mixture of $C_8$ aromatics from step g to the transalkylation zone. An embodiment of the invention is one, any or all of prior embodiments in this paragraph up through the first embodiment in this paragraph, wherein the transalkylation conditions include a temperature of about 320° C. to about 440° C. An embodiment of the invention is one, any or all of prior embodiments in this paragraph up through the first embodiment in this paragraph, wherein the first catalyst comprises at least one zeolitic component suitable for transalkylation, at least one zeolitic component suitable for dealkylation and at least one metal component suitable for hydrogenation. An embodiment of the invention is one, any or all of prior embodiments in this paragraph up through the first embodiment in this paragraph, wherein the toluene methylation product stream has a paraxylene to total xylene ratio of at least about 0.2, or preferably at least about 0.5, or more preferably about 0.8 to 0.95. Alternative embodiments describing processes and apparatuses for toluene methylation within an aromatics complex for producing paraxylene where no benzene byproduct is produced will be discussed in detail in the detailed description.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

Definitions

As used herein, the term "stream", "feed", "product", "part" or "portion" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

Hydrocarbon molecules may be abbreviated $C_1$, $C_2$, $C_3$, Cn where "n" represents the number of carbon atoms in the one or more hydrocarbon molecules or the abbreviation may be used as an adjective for, e.g., non-aromatics or compounds. Similarly, aromatic compounds may be abbreviated $A_6$, $A_7$, $A_8$, An where "n" represents the number of carbon atoms in the one or more aromatic molecules. Furthermore, a superscript "+" or "−" may be used with an abbreviated one or more hydrocarbons notation, e.g., $C_{3+}$ or $C_{3−}$, which is inclusive of the abbreviated one or more hydrocarbons. As an example, the abbreviation "$C_{3+}$" means one or more hydrocarbon molecules of three or more carbon atoms.

As used herein, the term "zone" or "unit" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally 50%, and preferably 70%, by mole, of a compound or class of compounds in a stream.

As depicted, process flow lines in the FIGURES can be referred to interchangeably as, e.g., lines, pipes, feeds, gases, products, discharges, parts, portions, or streams.

The term "feeding" means that the feed passes from a conduit or vessel directly to an object without passing through an intermediate vessel.

The term "passing" includes "feeding" and means that the material passes from a conduit or vessel to an object.

As used herein, the term "kilopascal" may be abbreviated "kPa" and the term "megapascal" may be abbreviated "MPa", and all pressures disclosed herein are absolute.

Figure 1:
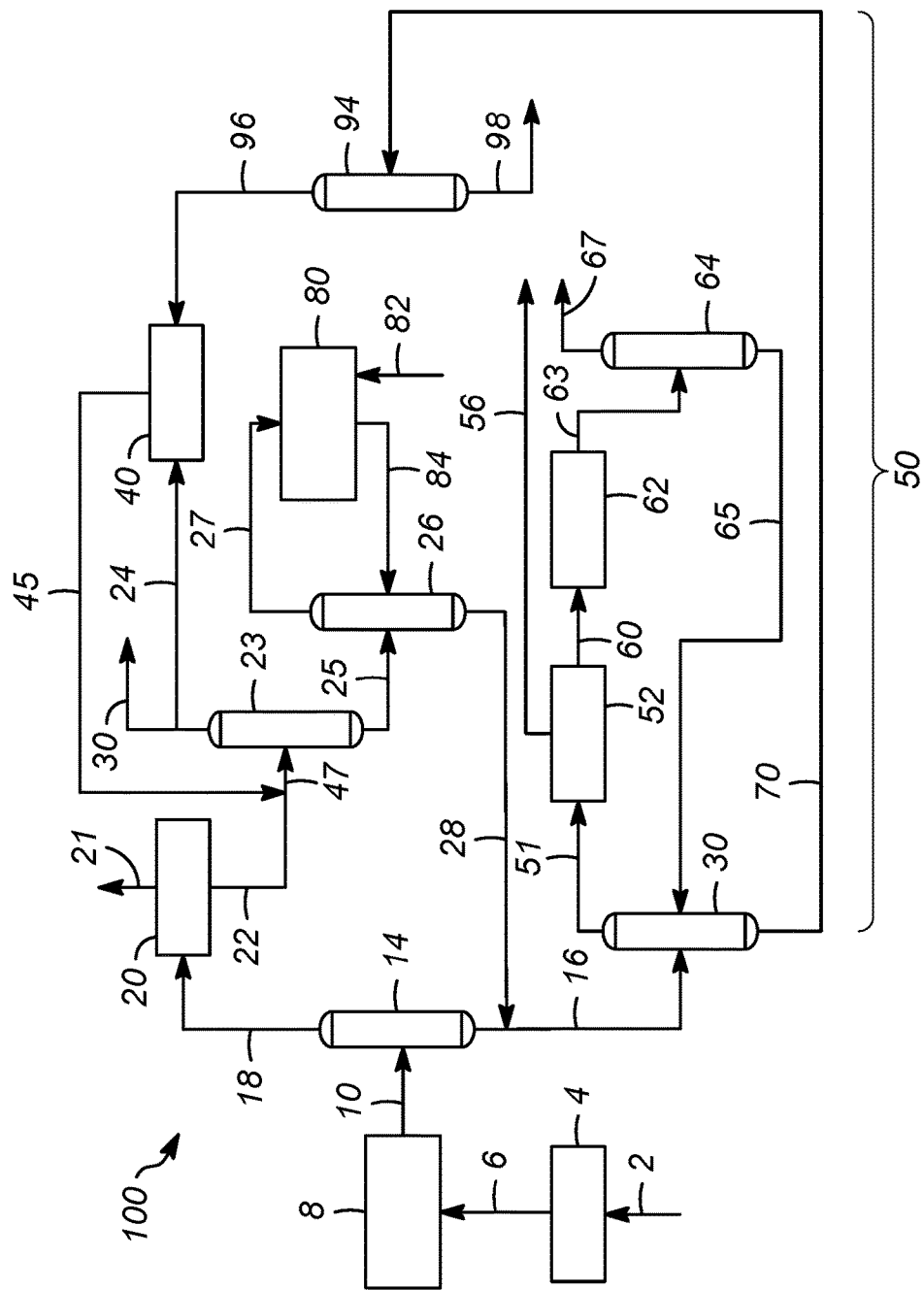
FIG. 1 illustrates an aromatics complex having an integrated toluene methylation zone.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

The following description is not to be taken in a limiting sense, but is made merely for the purpose of describing the general principles of exemplary aspects. The scope of the present disclosure should be determined with reference to the claims.

The feedstream to the present process generally comprises alkylaromatic hydrocarbons of the general formula $C_6H_{(6-n)}R_n$, where n is an integer from 0 to 5 and each R may be $CH_3$, $C_2H_5$, $C_3H_7$, or $C_4H_9$, in any combination. The aromatics-rich feed stream to the process of the present disclosure may be derived from a variety of sources, including without limitation catalytic reforming, steam pyrolysis of naphtha, distillates or other hydrocarbons to yield light olefins and heavier aromatics-rich byproducts (including gasoline-range material often referred to as "pygas"), and catalytic or thermal cracking of distillates and heavy oils to yield products in the gasoline range. Products from pyrolysis or other cracking operations generally will be hydrotreated according to processes well known in the industry before being charged to the complex in order to remove sulfur, olefins and other compounds which would affect product quality and/or damage catalysts or adsorbents employed therein. Light cycle oil from catalytic cracking also may be beneficially hydrotreated and/or hydrocracked according to known technology to yield products in the gasoline range; the hydrotreating preferably also includes catalytic reforming to yield the aromatics-rich feed stream. FIG. 1 is a simplified flow diagram of an exemplary aromatics-processing complex of the known art directed to the production of at least one xylene isomer. The complex may process an aromatics-rich feed which has been derived, for example, from catalytic reforming in a reforming zone 6. The reforming zone generally includes a reforming unit 4 that receives a feed via conduit 2. The reforming unit typically comprises a reforming catalyst. Usually such a stream will also be treated to remove olefinic compounds and light ends, e.g., butanes and lighter hydrocarbons and preferably pentanes; such removal, however, is not essential to the practice of the broad aspects of this disclosure and is not shown. The aromatics-containing feed stream contains benzene, toluene and $C_8$ aromatics and typically contains higher aromatics and aliphatic hydrocarbons including naphthenes.

Turning now to FIG. 1, an aromatics complex and process in accordance with one aspect wherein the aromatics complex includes an integrated toluene methylation zone will be illustrated and described. FIG. 1 is a simplified flow diagram of an exemplary aromatics-processing complex of the known art integrated with a toluene methylation unit directed to the production of at least one xylene isomer. The complex may process an aromatics-rich feed which has been derived, for example, from catalytic reforming in a reforming zone. The reforming zone generally includes a reforming unit that receives a feed. The reforming unit will typically comprise a reforming catalyst. Usually such a stream will also be treated to remove olefinic compounds and light ends, e.g., butanes and lighter hydrocarbons and preferably pentanes; such removal, however, is not essential to the practice of the broad aspects of this disclosure and is not shown. The aromatics-containing feed stream contains benzene, toluene and $C_8$ aromatics and typically contains higher aromatics and aliphatic hydrocarbons including naphthenes.

An embodiment of a process and apparatus for producing paraxylene in an aromatics complex is addressed with reference to a process and apparatus 100 illustrating an aromatics complex having an integrated toluene methylation scheme according to an embodiment as shown in FIG. 1. The process and apparatus 100 includes a hydrotreating zone 4, a naphtha splitter 14, a reforming zone 8, a reformate splitter 14, an aromatics extraction unit 20, a benzene column 23, a toluene column 26, a transalkylation zone 40, a toluene methylation unit 80, a xylene fractionation column 30, a heavy aromatics column 94, a para-xylene column 52, an isomerization column 62, and an isomerization deheptanizer column 64.

In accordance with an exemplary embodiment as shown in FIG. 1, a hydrocarbon feedstream in line 2 may be passed to the hydrotreating zone 4. In accordance with the instant embodiment as discussed, the hydrocarbon feedstream in line 2 is a naphtha stream and hence interchangeably referred to as naphtha stream in line 2. The naphtha stream in line 2 may be provided to the hydrotreating zone 4 to produce a hydrotreated naphtha stream in line 6. As used herein, the term "naphtha" means the hydrocarbon material boiling in the range between about 10° C. and about 200° C. atmospheric equivalent boiling point (AEBP) as determined by any standard gas chromatographic simulated distillation method such as ASTM D2887, all of which are used by the petroleum industry. The hydrocarbon material may be more contaminated and contain a greater amount of aromatic compounds than is typically found in refinery products. The typical petroleum derived naphtha contains a wide variety of different hydrocarbon types including normal paraffins, branched paraffins, olefins, naphthenes, benzene, and alkyl aromatics. Although the present embodiment is exemplified by a naphtha feedstream, the process is not limited to a naphtha feedstream, and can include any feedstream with a composition that overlaps with a naphtha feedstream.

Referring to FIG. 1, the hydrotreating zone 4 may include one or more hydrotreating reactors for removing sulfur and nitrogen from the naphtha stream in line 2. A number of reactions take place in the hydrotreating zone 4 including hydrogenation of olefins and hydrodesulfurization of mercaptans and other organic sulfur compounds; both of which (olefins, and sulfur compounds) are present in the naphtha fractions. Examples of sulfur compounds that may be present include dimethyl sulfide, thiophenes, benzothiophenes, and the like. Further, reactions in the hydrotreating zone 4 include removal of heteroatoms, such as nitrogen and metals. Conventional hydrotreating reaction conditions are employed in the hydrotreating zone 4 which are known to one of ordinary skill in the art.

The hydrotreated naphtha stream in line 6 withdrawn from the hydrotreating zone 4 may be passed to the catalytic reforming unit in the reforming zone 8 to provide a reformate stream in line 10. In an aspect, the hydrotreated naphtha stream in line 6 may be passed to the catalytic reforming unit 8 to provide the reformate stream in line 10.

The reforming conditions includes a temperature of from about 300° C. to about 500° C., and a pressure from about 0 kPa(g) to about 3500 kPa(g). Reforming catalysts generally comprise a metal on a support. This catalyst is conventionally a dual-function catalyst that includes a metal hydrogenation-dehydrogenation catalyst on a refractory support. The support can include a porous material, such as an inorganic oxide or a molecular sieve, and a binder with a weight ratio from 1:99 to 99:1. In accordance with various embodiments, the reforming catalyst comprises a noble metal comprising one or more of platinum, palladium, rhodium, ruthenium, osmium, and iridium. The reforming catalyst may be supported on refractory inorganic oxide support comprising one or more of alumina, a chlorided alumina a magnesia, a titania, a zirconia, a chromia, a zinc oxide, a thoria, a boria, a silica-alumina, a silica-magnesia, a chromia-alumina, an alumina-boria, a silica-zirconia and a zeolite.

The reformate feed stream is passed via conduit 10 to reformate splitter 14 and distilled to separate a stream comprising $C_8$ and heavier aromatics, withdrawn as a bottoms stream via a bottoms outlet in conduit 16, from toluene and lighter hydrocarbons recovered overhead via conduit 18. The toluene and lighter hydrocarbons are sent to extractive distillation process unit 20 which separates a largely aliphatic raffinate in conduit 21 from a benzene-toluene aromatics stream in conduit 22. The aromatics stream in conduit 22 is separated, along with stripped transalkylation product in conduit 45 which enters the benzene column 23 into a benzene stream in conduit 24 and a toluene-and-heavier aromatics stream in conduit 25 which is sent to a toluene column 26. The benzene stream in conduit 30 is a product stream. The benzene stream in conduit 24 is passed from the benzene column 23 to the transalkylation unit 40. In one embodiment, the transalkylation conditions may include a temperature of about 320° C. to about 440° C. The transalkylation zone may contain a first catalyst. In one embodiment, the first catalyst comprises at least one zeolitic component suitable for transalkylation, at least one zeolitic component suitable for dealkylation and at least one metal component suitable for hydrogenation. Toluene is recovered overhead from the toluene column 26 in conduit 27 and may be sent partially or totally to a toluene methylation unit 80 along with a methanol stream in conduit 82 as shown and discussed hereinafter.

The methanol stream in conduit 82 and the toluene in conduit 27 is passed to the toluene methylation unit 80 and produces a hydrocarbon stream in conduit 84. The hydrocarbon stream in conduit 84 is passed back to the toluene column 26. In one embodiment, the toluene methylation product stream has a paraxylene to total xylene ratio of at least about 0.2, or preferably at least about 0.5, or more preferably about 0.8 to 0.95.

The toluene column 26 produces a product stream in conduit 28 contains para-xylene, meta-xylene, ortho-xylene and ethylbenzene and passes via conduit 16 to para-xylene separation process 50. The separation process operates, preferably via adsorption employing a desorbent, to provide a mixture of para-xylene and desorbent via conduit 51 to extract column 52, which separates para-xylene from returned desorbent; the para-xylene may be purified in finishing column, yielding a para-xylene product via conduit 56.

The raffinate, comprising a non-equilibrium mixture of xylene isomers and ethylbenzene, is sent via conduit 60 to isomerization reactor 62. The raffinate is isomerized in reactor 62, which contains an isomerization catalyst to provide a product approaching equilibrium concentrations of $C_8$-aromatic isomers. In one embodiment, the isomerization conditions include a temperature of about 240° C. to about 440° C. Further, the isomerization zone includes a second catalyst. In one embodiment, the second catalyst comprises at least one zeolitic component suitable for xylene isomerization, at least one zeolitic component suitable for ethylbenzene conversion, and at least one metal component suitable for hydrogenation. In one embodiment, the isomerization process is carried out in the vapor phase. In yet another embodiment, the isomerization process is carried out in the liquid phase. In one embodiment, the isomerization process converts ethylbenzene by dealkylation to produce benzene. In another embodiment, the isomerization process converts ethylbenzene by isomerization to produce xylenes.

The product is passed via conduit 63 to deheptanizer 64, which removes $C_7$ and lighter hydrocarbons with bottoms passing via conduit 65 to xylene column 30 to separate $C_9$ and heavier materials from the isomerized $C_8$-aromatics. Overhead liquid from deheptanizer 64 is sent to a stripper, which removes light materials overhead in conduit 67 from $C_6$ and $C_7$ materials which are sent to the extractive distillation unit for recovery of benzene and toluene values.

The xylene column bottoms stream in line 70 may be passed to the heavy aromatics column 194 to separate heavy aromatics comprising $C_{11+}$ alkylaromatic hydrocarbons from $C_9$ and $C_{10}$ alkylaromatics recovered as the heavy aromatics column overhead stream in line 96. The $C_{11+}$ alkylaromatic hydrocarbons may be withdrawn from the heavy aromatics column 94 as a bottoms stream in line 98. The heavy aromatics column overhead stream in line 96 rich in $C_9$ and $C_{10}$ alkylaromatics may be blended with the benzene-enriched stream in line 24 to provide the transalkylation feed stream in line 24 which may be subsequently provide to the transalkylation zone 40 for production of additional xylenes and benzene as previously described.

There are many possible variations of this scheme within the known art, as the skilled routineer will recognize. For example, the entire $C_6$-$C_8$ reformate or only the benzene-containing portion may be subjected to extraction. Paraxylene may be recovered from a $C_8$-aromatic mixture by crystallization rather than adsorption. The separation zone may also contain a simulated moving bed adsorption unit. In one example, the simulated moving bed adsorption unit uses a desorbent with a lower boiling point than xylenes, such as toluene or benzene. In yet another embodiment, the simulated moving bed adsorption unit uses a desorbent with a higher boiling point than xylenes, such as paradiethylbenzene, paradiisopropylbenzene, tetralin, or paraethyltoluene. Meta-xylene as well as para-xylene may be recovered from a $C_8$-aromatic mixture by adsorption, and ortho-xylene may be recovered by fractionation. Alternatively, the $C_9$- and heavier stream or the heavy-aromatics stream is processed using solvent extraction or solvent distillation with a polar solvent or stripping with steam or other media to separate highly condensed aromatics as a residual stream from $C_9$+ recycle to transalkylation. In some cases, the entire heavy-aromatic stream may be processed directly in the transalkylation unit. The present disclosure is useful in these and other variants of an aromatics-processing scheme, aspects of which are described in U.S. Pat. No. 6,740,788 which is incorporated herein by reference.

Figure 2:
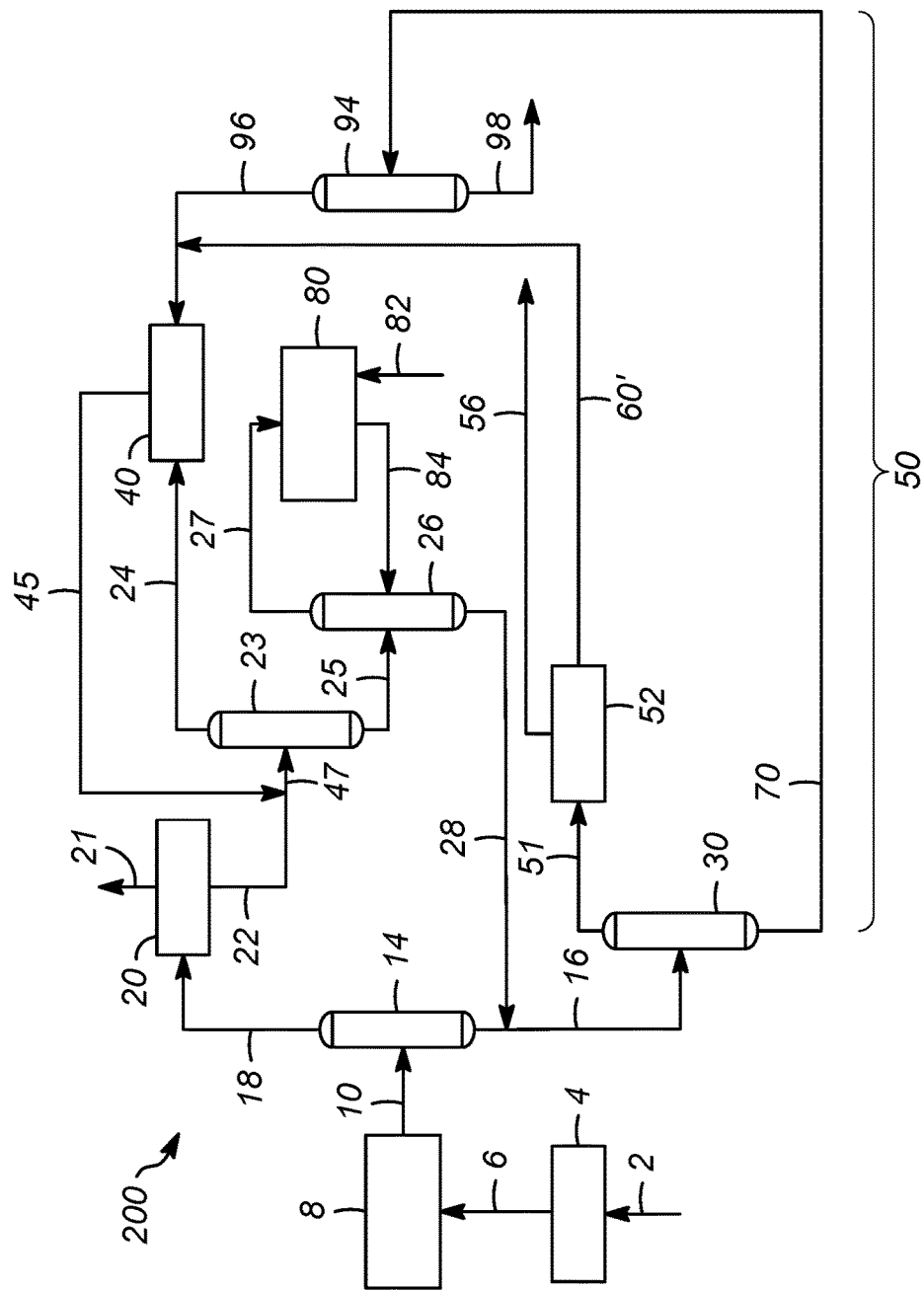
FIG. 2 illustrates another embodiment of an aromatics complex having an integrated toluene methylation zone.

Turning now to FIG. 2, another embodiment of the aromatics complex is addressed with reference to a process and apparatus 200 providing an alternative integrated toluene methylation scheme. Many of the elements in FIG. 2 have the same configuration as in FIG. 1 and bear the same respective reference number and have similar operating conditions. Elements in FIG. 2 that correspond to elements in FIG. 1 but have a different configuration bear the same reference numeral as in FIG. 1 but are marked with a prime symbol ('). Further, the temperature, pressure and composition of various streams are similar to the corresponding streams in FIG. 1, unless specified otherwise. The apparatus and process in FIG. 2 are the same as in FIG. 1 with the exception of the noted following differences. In accordance with the exemplary embodiment as shown in the FIG. 2, the paraxylene raffinate comprising a non-equilibrium mixture of xylene isomers and ethylbenzene n line 60' exits the paraxylene column 52 and is directed to the heavy aromatics column 94 overhead in conduit 96 to be directed into the transalkylation unit 40. As illustrated in FIG. 2, there is no isomerization zone or deheptanizer 64. The benefits of this configuration include the elimination of some equipment (reduced capital expense) and reduction in operating expense (energy/utility consumption). The process may increase the amount of paraxylene that can be produced form a given amount of reformate. The process may also reduce the amount of reformate required to produce a fixed amount of paraxylene. Further, the process may avoid the production of benzene as a byproduct from the aromatics complex.

Figure 3:
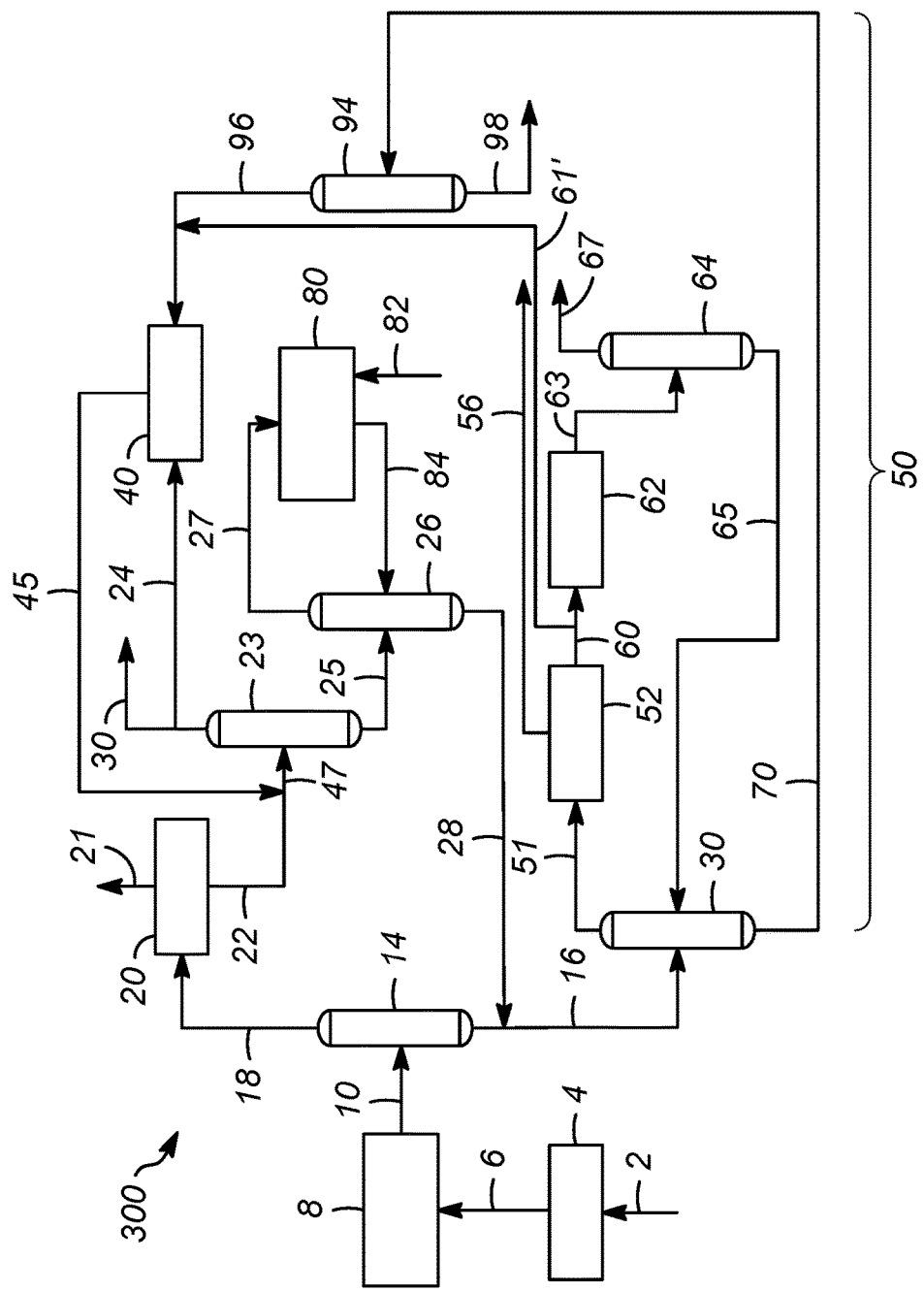
FIG. 3 illustrates yet another embodiment of an aromatics complex having an integrated toluene methylation zone.

Turning now to FIG. 3, another embodiment of the aromatics complex is addressed with reference to a process and apparatus 300 providing an alternative integrated toluene methylation scheme. Many of the elements in FIG. 3 have the same configuration as in FIG. 1 and bear the same respective reference number and have similar operating conditions. Elements in FIG. 3 that correspond to elements in FIG. 1 but have a different configuration bear the same reference numeral as in FIG. 1 but are marked with a prime symbol ('). Further, the temperature, pressure and composition of various streams are similar to the corresponding streams in FIG. 1, unless specified otherwise. The apparatus and process in FIG. 3 are the same as in FIG. 1 with the exception of the noted following differences. In accordance with the exemplary embodiment as shown in the FIG. 3, a portion of the paraxylene raffinate comprising a non-equilibrium mixture of xylene isomers and ethylbenzene in line 61' exits the paraxylene column 52 and is directed to the heavy aromatics column 94 overhead in conduit 96 to be directed into the transalkylation unit 40. The As illustrated in FIG. 2, the remaining portion of conduit 60 remains connected to the isomeraztion unit 62 which is then connected to the dehepanizer 64. The benefits of this configuration include the fact that the process may increase the amount of paraxylene that can be produced form a given amount of reformate. Further, the process may also reduce the amount of reformate required to produce a fixed amount of paraxylene. Finally, the process may avoid the production of benzene as a byproduct from the aromatics complex.

Figure 4:
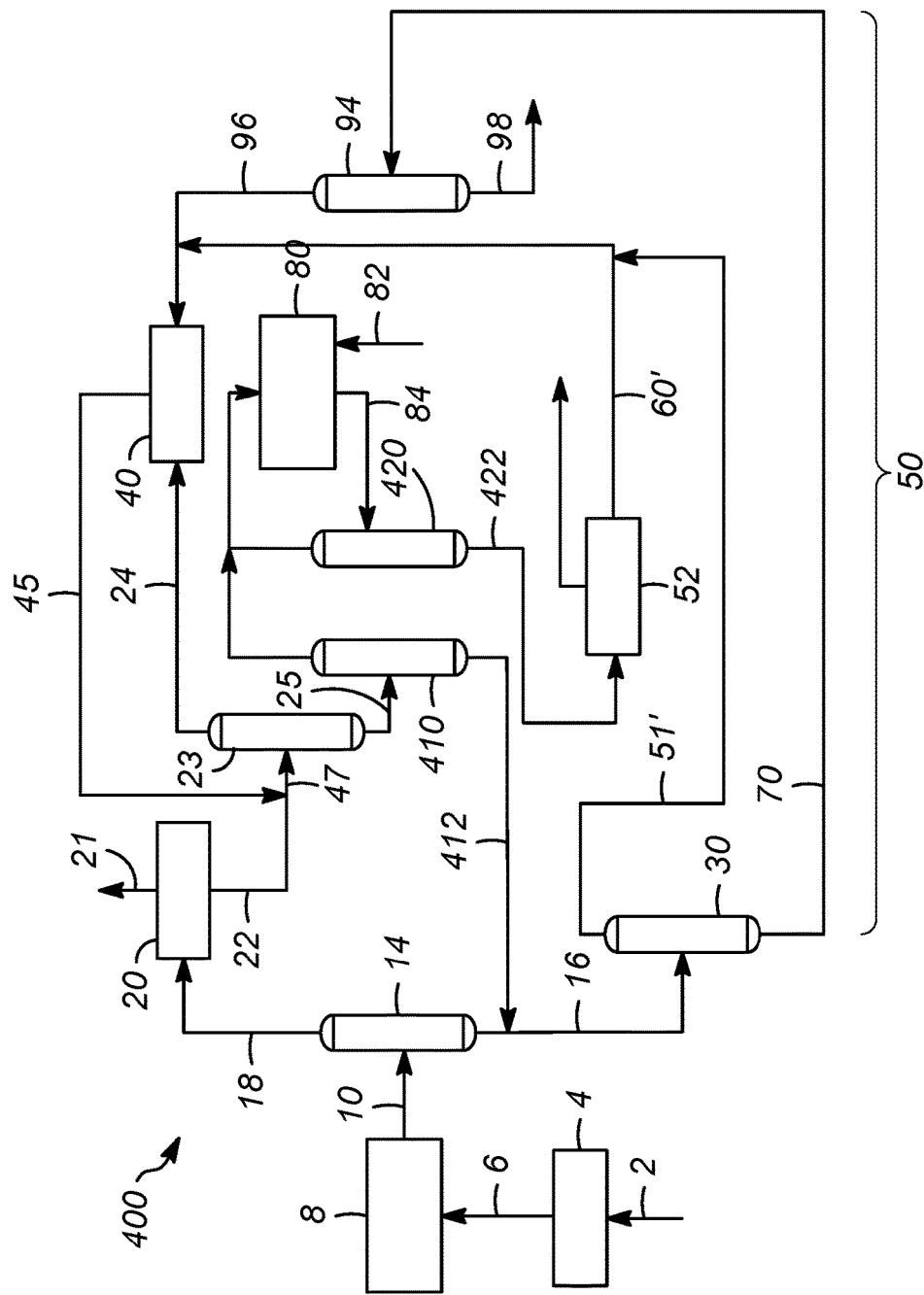
FIG. 4 illustrates another embodiment of an aromatics complex having an integrated toluene methylation zone.

Turning now to FIG. 4, another embodiment of the aromatics complex is addressed with reference to a process and apparatus 400 providing an alternative integrated toluene methylation scheme. Many of the elements in FIG. 4 have the same configuration as in FIG. 1 and bear the same respective reference number and have similar operating conditions. Elements in FIG. 4 that correspond to elements in FIG. 1 but have a different configuration bear the same reference numeral as in FIG. 1 but are marked with a prime symbol ('). Further, the temperature, pressure and composition of various streams are similar to the corresponding streams in FIG. 1, unless specified otherwise. The apparatus and process in FIG. 4 are the same as in FIG. 1 with the exception of the noted following differences. In accordance with the exemplary embodiment as shown in the FIG. 4, there are two toluene columns. The first toluene column 410 produces equilibrium xylenes in conduit 412 and the second toluene column 420 produces rich paraxylene and xylenes in conduit 422. In FIG. 4, conduit 422 is directed to the paraxylene column 52, whereas conduit 51' is directed to be coupled to conduit 60' which is then directed to conduit 96 to be directed into the transalkylation unit 40. The benefits of this configuration include the reduction in key equipment size saving capital and operating expense. It should be noted that various changes and modifications to the presently preferred embodiments described herein will be apparent to those skilled in the art. Such changes and modifications may be made without departing from the spirit and scope of the present subject matter and without diminishing its attendant advantages.

Specific Embodiments

While the following is described in conjunction with specific embodiments, it will be understood that this description is intended to illustrate and not limit the scope of the preceding description and the appended claims.

A first embodiment of the invention is a process for producing paraxylene with no benzene byproduct, comprising passing a lighter aromatic stream containing benzene and a heavier aromatic stream containing $C_9$-$C_{10}$ aromatic compounds to a transalkylation zone; subjecting the lighter aromatic stream and the heavier aromatic stream in the transalkylation zone to transalkylation conditions including the presence of a first catalyst to provide a transalkylation product stream having a greater concentration of toluene to $C_8$ aromatics; separating by fractionation from the transalkylation product stream a first boiling fraction comprising benzene, a second boiling fraction comprising toluene, a third boiling fraction comprising $C_8$ aromatics and a fourth boiling fraction comprising $C_{9+}$ aromatics; recycling at least a portion of the benzene from the transalkylation product stream back to the transalkylation zone; passing at least a portion of the second boiling fraction from steps c, g and i and a methanol stream to a toluene methylation zone operating under toluene methylation conditions to produce a toluene methylation product stream; separating by fractionation from the toluene methylation product stream the same fractions described in step c; subjecting at least a portion of the third boiling fraction comprising $C_8$ aromatics of steps c, g and i to a separation zone to selectively remove a paraxylene product and provide a non-equilibrium mixture of $C_8$ aromatics; passing the non-equilibrium mixture of $C_8$ aromatics from step g to the transalkylation zone. An embodiment of the invention is one, any or all of prior embodiments in this paragraph up through the first embodiment in this paragraph, wherein the transalkylation conditions include a temperature of about 320° C. to about 440° C. An embodiment of the invention is one, any or all of prior embodiments in this paragraph up through the first embodiment in this paragraph, wherein the first catalyst comprises at least one zeolitic component suitable for transalkylation, at least one zeolitic component suitable for dealkylation and at least one metal component suitable for hydrogenation. An embodiment of the invention is one, any or all of prior embodiments in this paragraph up through the first embodiment in this paragraph, wherein the toluene methylation product stream has a paraxylene to total xylene ratio of at least about 0.2, or preferably at least about 0.5, or more preferably about 0.8 to 0.95.

A second embodiment of the invention is a process for producing paraxylene with no benzene byproduct, comprising passing a lighter aromatic stream containing benzene and a heavier aromatic stream containing $C_9$-$C_{10}$ aromatic compounds to a transalkylation zone; subjecting the lighter aromatic stream and the heavier aromatic stream in the transalkylation zone to transalkylation conditions including the presence of a first catalyst to provide a transalkylation product stream having a greater concentration of toluene to $C_8$ aromatics; separating by fractionation from the transalkylation product stream a first boiling fraction comprising benzene, a second boiling fraction comprising toluene, a third boiling fraction comprising $C_8$ aromatics and a fourth boiling fraction comprising $C_{9+}$ aromatics; recycling at least a portion of the benzene from the transalkylation product stream back to the transalkylation zone; passing at least a portion of the second boiling fraction from steps c, g and i and a methanol stream to a toluene methylation zone operating under toluene methylation conditions to produce a toluene methylation product stream; separating by fractionation from the toluene methylation product stream the same fractions described in step c; subjecting at least a portion of the third boiling fraction comprising $C_8$ aromatics of steps c, g and i to a separation zone to selectively remove a paraxylene product and provide a non-equilibrium mixture of $C_8$ aromatics; subjecting a portion of the non-equilibrium mixture of $C_8$ aromatics to xylene isomerization conditions including the presence of a second catalyst to provide an isomerization product; passing a portion of the non-equilibrium mixture of C8 aromatics form step g to the transalkylation zone; and separating by fractionation from the isomerization product stream the same fractions described in step c. An embodiment of the invention is one, any or all of prior embodiments in this paragraph up through the second embodiment in this paragraph, wherein the transalkylation conditions include a temperature of about 320° C. to about 440° C. An embodiment of the invention is one, any or all of prior embodiments in this paragraph up through the second embodiment in this paragraph, wherein the first catalyst comprises at least one zeolitic component suitable for transalkylation, at least one zeolitic component suitable for dealkylation and at least one metal component suitable for hydrogenation. An embodiment of the invention is one, any or all of prior embodiments in this paragraph up through the second embodiment in this paragraph, wherein the toluene methylation product stream has a paraxylene to total xylene ratio of at least about 0.2, or preferably at least about 0.5, or more preferably about 0.8 to 0.95. An embodiment of the invention is one, any or all of prior embodiments in this paragraph up through the second embodiment in this paragraph, wherein the isomerization conditions include a temperature of about 240° C. to about 440° C. An embodiment of the invention is one, any or all of prior embodiments in this paragraph up through the second embodiment in this paragraph, wherein the second catalyst comprises at least one zeolitic component suitable for xylene isomerization, at least one zeolitic component suitable for ethylbenzene conversion, and at least one metal component suitable for hydrogenation. An embodiment of the invention is one, any or all of prior embodiments in this paragraph up through the second embodiment in this paragraph, wherein the isomerization process is carried out in the vapor phase. An embodiment of the invention is one, any or all of prior embodiments in this paragraph up through the second embodiment in this paragraph, wherein the isomerization process converts ethylbenzene by dealkylation to produce benzene. An embodiment of the invention is one, any or all of prior embodiments in this paragraph up through the second embodiment in this paragraph, wherein the isomerization process converts ethylbenzene by isomerization to produce xylenes. An embodiment of the invention is one, any or all of prior embodiments in this paragraph up through the second embodiment in this paragraph, wherein the isomerization process is carried out in the liquid phase.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for producing paraxylene with no benzene byproduct, comprising:
    a) passing a lighter aromatic stream containing benzene and a heavier aromatic stream containing $C_9$-$C_{10}$ aromatic compounds to a transalkylation zone;
    b) subjecting the lighter aromatic stream and the heavier aromatic stream in the transalkylation zone to transalkylation conditions including the presence of a first catalyst to provide a transalkylation product stream having a greater concentration of toluene to $C_8$ aromatics;
    c) separating by fractionation from the transalkylation product stream a first boiling fraction comprising benzene, a second boiling fraction comprising toluene, a third boiling fraction comprising $C_8$ aromatics and a fourth boiling fraction comprising $C_{9+}$ aromatics;
    d) recycling at least a portion of the benzene from the transalkylation product stream back to the transalkylation zone;
    e) passing at least a portion of the second boiling fraction from steps c, g and i and a methanol stream to a toluene methylation zone operating under toluene methylation conditions to produce a toluene methylation product stream;
    f) separating by fractionation from the toluene methylation product stream the same fractions described in step c;
    g) subjecting at least a portion of the third boiling fraction comprising $C_8$ aromatics of steps c, g and i to a separation zone to selectively remove a para-xylene product and provide a non-equilibrium mixture of $C_8$ aromatics; and
    h) passing the non-equilibrium mixture of $C_8$ aromatics from step g to the transalkylation zone.

2. The process according to claim 1, wherein the transalkylation conditions include a temperature of about 320° C. to about 440° C.

3. The process according to claim 1, wherein the first catalyst comprises at least one zeolitic component suitable for transalkylation, at least one zeolitic component suitable for dealkylation and at least one metal component suitable for hydrogenation.

4. The process according to claim 1, wherein the toluene methylation product stream has a paraxylene to total xylene ratio of at least about 0.2.

5. A process for producing paraxylene with no benzene byproduct, comprising:
    a) passing a lighter aromatic stream containing benzene and a heavier aromatic stream containing $C_9$-$C_{10}$ aromatic compounds to a transalkylation zone;
    b) subjecting the lighter aromatic stream and the heavier aromatic stream in the transalkylation zone to transalkylation conditions including the presence of a first catalyst to provide a transalkylation product stream having a greater concentration of toluene to $C_8$ aromatics;
    c) separating by fractionation from the transalkylation product stream a first boiling fraction comprising benzene, a second boiling fraction comprising toluene, a third boiling fraction comprising $C_8$ aromatics and a fourth boiling fraction comprising $C_{9+}$ aromatics;
    d) recycling at least a portion of the benzene from the transalkylation product stream back to the transalkylation zone;
    e) passing at least a portion of the second boiling fraction from steps c, g and i and a methanol stream to a toluene methylation zone operating under toluene methylation conditions to produce a toluene methylation product stream;
    f) separating by fractionation from the toluene methylation product stream the same fractions described in step c;
    g) subjecting at least a portion of the third boiling fraction comprising $C_8$ aromatics of steps c, g and i to a separation zone to selectively remove a para-xylene product and provide a non-equilibrium mixture of $C_8$ aromatics;
    h) subjecting a portion of the non-equilibrium mixture of $C_8$ aromatics to xylene isomerization conditions including the presence of a second catalyst to provide an isomerization product;
    i) passing a portion of the non-equilibrium mixture of C8 aromatics form step g to the transalkylation zone; and
    j) separating by fractionation from the isomerization product stream the same fractions described in step c.

6. The process according to claim 5, wherein the transalkylation conditions include a temperature of about 320° C. to about 440° C.

7. The process according to claim 5, wherein the first catalyst comprises at least one zeolitic component suitable for transalkylation, at least one zeolitic component suitable for dealkylation and at least one metal component suitable for hydrogenation.

8. The process according to claim 5, wherein the toluene methylation product stream has a paraxylene to total xylene ratio of at least about 0.2.

9. The process according to claim 5, wherein the isomerization conditions include a temperature of about 240° C. to about 440° C.

10. The process according to claim 5, wherein the second catalyst comprises at least one zeolitic component suitable for xylene isomerization, at least one zeolitic component suitable for ethylbenzene conversion, and at least one metal component suitable for hydrogenation.

11. The process according to claim 5, wherein the isomerization process is carried out in the vapor phase.

12. The process according to claim 5, wherein the isomerization process converts ethylbenzene by dealkylation to produce benzene.

13. The process according to claim 5, wherein the isomerization process converts ethylbenzene by isomerization to produce xylenes.

14. The process according to claim 5, wherein the isomerization process is carried out in the liquid phase.

15. The process according to claim 1, wherein the toluene methylation product stream has a paraxylene to total ratio of at least about 0.5.

16. The process according to claim 1, wherein the toluene methylation product stream has a paraxylene to total ratio of at least about 0.8 to 0.95.

17. The process according to claim 5, wherein the toluene methylation product stream has a paraxylene to total ratio of at least about 0.5.

18. The process according to claim 5, wherein the toluene methylation product stream has a paraxylene to total ratio of at least about 0.8 to 0.95.

* * * * *